US011602616B2

(12) United States Patent
Teoh (10) Patent No.: US 11,602,616 B2
(45) Date of Patent: Mar. 14, 2023

(54) ADHESIVE ENCASED PROTECTIVE CAPS FOR NEEDLE DEVICES AND RELATED METHODS

(71) Applicant: B. Braun Melsungen AG, Melsungen (DE)

(72) Inventor: Hui Kuun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 9 days.

(21) Appl. No.: 16/619,316

(22) PCT Filed: Jun. 8, 2018

(86) PCT No.: PCT/EP2018/065128
§ 371 (c)(1),
(2) Date: Dec. 4, 2019

(87) PCT Pub. No.: WO2018/224637
PCT Pub. Date: Dec. 13, 2018

(65) Prior Publication Data
US 2020/0094024 A1  Mar. 26, 2020

Related U.S. Application Data

(60) Provisional application No. 62/517,415, filed on Jun. 9, 2017.

(51) Int. Cl.
*A61M 25/06* (2006.01)
*A61M 25/02* (2006.01)
(Continued)

(52) U.S. Cl.
CPC ........ *A61M 25/0618* (2013.01); *A61M 25/02* (2013.01); *A61M 25/0606* (2013.01);
(Continued)

(58) Field of Classification Search
CPC ........ A61M 2005/312; A61M 25/0618; A61M 39/16; A61M 5/3202; A61M 35/003;
(Continued)

(56) References Cited

U.S. PATENT DOCUMENTS 3,270,743 A * 9/1966 Gingras ............ A61M 5/3202
604/199
4,693,708 A * 9/1987 Wanderer ............ A61M 5/3271
604/263
(Continued)

FOREIGN PATENT DOCUMENTS

| CN | 101257941 A | 9/2008 |
| CN | 104023768 A | 9/2014 |
| WO | WO 2016/059172 A1 | 4/2016 |

OTHER PUBLICATIONS

International Search Report and Written Opinion on corresponding PCT application (PCT/EP2018/065128) from International Searching Authority (EPO) dated Aug. 22, 2018.
(Continued)

*Primary Examiner* — Bhisma Mehta
*Assistant Examiner* — Robert F Allen
(74) *Attorney, Agent, or Firm* — KOS IP Law LLP (57) ABSTRACT

A needle assembly includes a catheter hub, a catheter tube extending distally from the catheter hub, and a needle hub having a needle having a needle tip extending out the catheter tube. A protective cap is positioned with the catheter hub and covers the catheter tube and the needle tip. The protective cap has a casing having a casing body, a first opening at a proximal end of the casing body, a proximal cavity having the needle tip and the catheter tube located in the proximal cavity, a second opening at an end opposite the first opening and opening into a distal cavity, and a rim at the second opening. A lid is removably attached to the rim at the second opening to seal a solution inside the distal cavity. The
(Continued)

solution is dispensable from the distal cavity following separation of the lid from the rim.

22 Claims, 5 Drawing Sheets

(51) Int. Cl.
*A61M 35/00* (2006.01)
*A61F 13/40* (2006.01)

(52) U.S. Cl.
CPC .......... *A61M 35/003* (2013.01); *A61M 35/006* (2013.01); *A61M 2025/0253* (2013.01)

(58) Field of Classification Search
CPC ................ A61M 39/162; A61M 5/001; A61M 25/0606; A61M 35/006; A61M 2025/0253; A61M 25/02
See application file for complete search history.

(56) References Cited

U.S. PATENT DOCUMENTS

| | | | |
|---|---|---|---|
| 6,315,113 B1 | 11/2001 | Britton et al. | |
| 7,032,632 B2 * | 4/2006 | Shingle | B65D 51/246 141/381 |
| 7,699,810 B2 * | 4/2010 | Rosenberg | A61M 25/02 604/180 |
| 8,091,746 B2 * | 1/2012 | Gotler | B65D 41/3447 222/569 |
| 9,259,535 B2 * | 2/2016 | Anderson | A61M 39/16 |
| 2004/0112510 A1 | 6/2004 | Rosenberg | |
| 2007/0038184 A1 * | 2/2007 | Bialecki | A61M 25/0618 604/110 |
| 2014/0008366 A1 | 1/2014 | Genosar | |
| 2017/0157332 A1 * | 6/2017 | Nguyen | A61M 5/31511 |

OTHER PUBLICATIONS

International Preliminary Report on Patentability (Chapter I) on corresponding PCT application (PCT/EP2018/065128) from International Searching Authority (EPO) dated Dec. 19, 2019.
Office Action including Search Report on related foreign application (CN Application No. 201880051497.6) from the National Intellectual Property Administration, P.R. China dated Jul. 9, 2021.
Decision of Rejection on related foreign application (CN Application No. 201880051497.6) from the National Intellectual Property Administration, P.R. China dated May 23, 2022.

* cited by examiner

ADHESIVE ENCASED PROTECTIVE CAPS FOR NEEDLE DEVICES AND RELATED METHODS

FIELD OF ART

The present disclosure generally relates to needle devices and more specifically to protective caps for needle devices having adhesive stored in the protective cap for use to secure the catheter following successful venipuncture and related methods.

BACKGROUND

Intravenous ("IV") catheter assemblies or needle devices are common medical invasive devices routinely used for a variety of infusion therapies, including infusing a patient with fluids, withdrawing blood from a patient, or monitoring various parameters of the patient's vascular system. The IV catheter assemblies are inserted in a majority of all hospitalized patients during their hospital stay and frequently initiated in many emergency situations.

The IV catheter assemblies use needles with sharp tips that are typically covered by a cap during packaging of the catheter assemblies. The sharp tip of such a needle poses a safety hazard that is often overcome by the inclusion of a removable protective cap or cover that covers the needle tip and at least part of the assembly, in a thermoplastic wrap or a vacuum pack. After removal from the packaging material, and prior to insertion of the needle and catheter into the patient, the cap is often removed and discarded.

Insertion procedure for an IV catheter assembly contains four basic steps after removing the protective cap: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand to slow down or stop the flow of blood through the catheter; and (4) the healthcare worker then tapes the exposed end of the catheter or the catheter hub to the patient's skin and connects it to the source of the fluid to be administered into the patient's vein.

There is a very high failure rate for catheters, mainly due to inadequate fixation of the catheter to the patient's skin. For example, the catheter may be pulled out accidentally by the patient or hospital staff or simply fall out potentially causing blood to leak onto the patient's skin, clothing, or bed, which can cause patient distress, infection, and potential health risks to hospital staff coming into contact with the blood. Additionally, insertion of a replacement catheter can be unpleasant or painful. Thus, significant reduction in intravenous catheter failure rates is expected to have beneficial effects on patient comfort and outcomes, along with hospital flow and costs.

SUMMARY

Aspects of the present disclosure include needle assemblies or devices and related methods of forming and using the needle assemblies and components thereof.

An exemplary needle assembly can be a needle device or an IV catheter assembly. The needle assembly can also be an over-the-needle catheter assembly.

The needle device can have configurations as described in the various embodiments or can be varied by incorporating features from the described embodiments.

In an example, the needle assembly can comprise a first hub or catheter hub, a catheter tube extending distally from the catheter hub and a second hub or needle hub having a needle having a needle tip extending out the catheter tube, and a protective cap positioned with the catheter hub and covering the catheter tube and the needle tip.

The protective cap can be firmly connected to the needle device by frictional engagement and/or positive engagement.

The catheter tube can have a lumen or bore for receiving the needle and has a distal opening or distal end opening.

The needle can have a needle tip and can include a change in profile located proximal of the tip for use with a needle guard.

The needle tip can extend distally of the distal end opening of the catheter tube in the ready to use position with the change in profile for use with a needle guard located proximally of the distal tube opening.

The change in profile can be an enlarged section, such as a crimp, a bump, or a material build-up having a different profile than other diameter sections of the needle shaft.

The change in profile can be used to interact with an opening through a wall of a needle guard during retraction of the needle.

The needle guard can be provided in the interior cavity of the first hub for covering the needle tip in the protective position.

In an example, the needle guard can include a proximal wall and two arms extending distally of the proximal wall. The two arms can intersect one another in the ready to use position and in the protective position in which the needle guard covers the needle tip, and as viewed from a side. In some examples, the two arms of the needle guard can extend in a distal direction without intersecting one another.

The protective cap can comprise a casing having a casing body, a first opening at a proximal end, a needle cavity having the needle tip and the catheter tube located therein, a second opening at a distal end opening into an adhesive cavity, and a rim at the second opening.

A lid can be removably attached to the rim at the second opening to seal an adhesive solution inside the adhesive cavity.

The adhesive solution can be dispensable from the adhesive cavity following removal of the lid.

The adhesive solution can be in an uncured form.

The needle cavity can be separated from the adhesive cavity by a barrier.

A spout can project radially outwardly from the adhesive cavity to facilitate application of the adhesive to the patient.

The lid can be a thin film comprising a sealing body and a tab projecting from the sealing body. The tab can be sized and shaped to provide a gripping surface for a user to peel the lid from the protective cap prior to adhesive application.

The tab can have a rough texture on opposite surfaces of the tab.

The lid can comprise a cover removably attached to the rim at the second opening and a handle extending from an outside surface of the cover.

The handle can have concave surfaces at an end.

A base can extend from an inside surface of the cover and into the adhesive cavity.

The base of the lid can be scallop shaped to enable scooping of the adhesive solution out from the adhesive cavity.

The adhesive cavity can comprise a wall structure defining an adhesive holder attached to the casing body.

Another aspect of the present disclosure can include a protective cap located with a needle device. The protective cap can comprise a casing having a casing body, a first opening at a proximal end, a needle cavity to having a needle tip and a catheter tube located therein, a second opening at a distal end opening into an adhesive cavity, and a rim at the second opening.

A lid can be removably attached to the rim at the second opening to seal an adhesive solution inside the adhesive cavity.

The adhesive solution can be dispensable from the adhesive cavity following removal of the lid.

A barrier can separate the needle cavity from the adhesive cavity.

A spout can project radially outwardly from the adhesive cavity to facilitate application of the adhesive to the patient.

The lid can be a thin film comprising a sealing body and a tab projecting from the sealing body.

The tab can be sized and shaped to provide a gripping surface for a user to peel the lid from the protective cap prior to adhesive application.

The tab can have a rough texture on opposite surfaces of the tab.

The lid can comprise a cover removably attached to the rim at the second opening, and a handle extending from an outside surface of the cover.

The handle can have concave surfaces on an end.

A base can extend from an inside surface of the cover and into the adhesive cavity.

The base of the lid can be scallop shaped to enable scooping of the adhesive solution out from the adhesive cavity.

The adhesive cavity can comprise a wall structure defining an adhesive holder attached to the casing body.

The needle device can comprise a catheter hub, a catheter tube extending distally from the catheter hub, and a needle hub having a needle having a needle tip extending out the catheter tube.

Another aspect of the present disclosure includes a method of securing a catheter tube of a needle assembly to a patient. The method can comprise detaching a protective cap from the needle assembly to uncover a catheter tube and a needle tip, inserting the catheter tube and a needle having the needle tip extending out the catheter tube into a patient, removing the needle from the patient, removing a lid removably attached to the rim at the second opening to access an adhesive solution sealed inside the adhesive cavity, and dispensing the adhesive solution from the adhesive cavity to the catheter tube and the patient to secure the catheter tube to the patient.

The protective cap comprise a casing having a casing body, a first opening at a proximal end, a needle cavity having the needle tip and the catheter tube locate therein, a second opening at a distal end opening into an adhesive cavity, and a rim at the second opening.

The adhesive solution can be dispensed from the adhesive cavity by tilting the protective cap so that the adhesive flows out of the adhesive cavity under gravity.

The adhesive solution can be removed from the adhesive cavity by scooping out the adhesive solution using the lid.

A further aspect of the present invention can include a needle assembly, said needle assembly can comprise: a catheter hub, a catheter tube extending distally from the catheter hub and a needle hub having a needle having a needle tip extending out a distal end of the catheter tube; a protective cap positioned at least partly over the catheter hub and covering the catheter tube and the needle tip, the protective cap comprising: a casing having a casing body, a first opening at a proximal end, a proximal cavity having the needle tip and the catheter tube located therein, a second opening remote from the first opening and opening into a distal cavity, and a rim at the second opening; and a lid removably attached at the second opening to seal in a solution inside the distal cavity; and wherein the solution is dispensable from the distal cavity following separation of the lid from the casing body.

The protective cap can be positioned at least partly around or over the catheter hub by having a cutout at a proximal section that can accommodate wings on the catheter hub.

The storage cavity or holder of the protective cap can be located remotely, such as being spaced apart, from the proximal opening. The storage cavity or holder can be located at a distal end of the casing body of the protective cap.

A barrier can separate the proximal cavity from the distal cavity.

A spout can be provided at the distal cavity to facilitate application or dispensing of the solution to the patient.

The lid can be a thin film comprising a sealing body and a tab projecting from the sealing body; said tab can be sized and shaped to provide a gripping surface for a user to peel the lid from the protective cap prior to application of the solution.

The tab can have a rough texture on opposite surfaces of the tab.

The lid can comprise a cover removably attached to the rim at the second opening and a handle extending from an outside surface of the cover.

A base of the lid can have a scallop shape to enable scooping of the solution out from the distal cavity.

A still further aspect of the present invention can include a protective cap positioned with a needle device, the protective cap can comprise: a casing having a casing body, a first opening at a proximal end, a proximal cavity having a needle and with a tip located therein, a second opening remoted from the first opening and opening into a distal cavity, and a rim at the second opening; a lid removably attached at the second opening to seal in a solution inside the distal cavity; and wherein the solution is dispensable from the distal cavity following separation of the lid from the casing body.

A still yet further aspect of the present disclosure is a method of manufacturing a needle assembly. The method can comprise: forming a catheter hub and attaching a catheter tube having a distal opening to the catheter hub; coupling a needle hub having a needle having a needle tip to the catheter hub so that the needle tip extends out the distal end of the catheter tube; placing a protective cap at least partly over the catheter hub and covering the catheter tube and the needle tip, the protective cap comprising: a casing having a casing body, a first opening at a proximal end, a proximal cavity having the needle tip and the catheter tube located therein, a second opening remote from the first opening and opening into an distal cavity, and a rim at the second opening; and a lid removably attached at the second opening to seal in a solution inside the distal cavity; and wherein the solution is dispensable from the distal cavity following separation of the lid from the casing body.

The method can include incorporating a needle guard about or around the needle to cover the needle tip in a used position, such as after removal of the needle following successful venipuncture.

A protective cap described herein can be assembled to the needle device or needle assembly by engaging or gripping a feature on the needle device, such as a feature on the catheter hub, the needle hub, or both, to secure the protective cap to the needle device.

The protective cap can prevent accidental contact with the needle tip and can prevent the needle hub from detaching from the catheter hub prior to use, such as from premature separation. In an example, the protective cap can engage or grip the flange or tab of the needle hub. The protective cap can be provided with the needle device when the needle device is in its product packaging, such as peelable plastic shell or blister package.

When the needle device is ready for use, the needle device and protective cap can first be removed from the product packaging then the protective cap can be removed from the needle device by pulling the protective cap and the needle device away from each other until a sufficient pulling force is reached to overcome the engagement between the protective cap and the needle device. With the protective cap separated from the needle device, the needle tip and the catheter tube can then be exposed and ready for a user to access the vasculature of the patient.

The point of insertion of the needle and catheter tube through the skin of the patient is known as an insertion point. After a successful venipuncture, the needle hub can be retracted proximally away from the catheter hub to remove the needle from the patient with the catheter tube remaining implanted in the peripheral vein of the patient. Typically, a conventional protective cap is discarded once removed from the needle device. However, the protective cap described herein can be retained and used after venipuncture.

The protective cap of the present disclosure can both protect a person from unwanted needle sticks and serve as a storage unit for storing a solution, fluid, or an object. The storage unit can have a lid to seal in the solution or object for storing. The lid can be peelable from the protective cap or twistable to separate from the protective cap.

The protective cap can include three components, namely an outer casing, adhesive, fluid, or object carried by the storage unit of the protective cap, and a seal or lid for closing in the opening of the storage unit, which can also be called a cavity holder or distal cavity. In an example, the outer casing can have a body defining an interior space for accommodating the needle and a storage space, unit or cavity for carrying the fluid.

The adhesive fluid or solution can be carried in a cavity or holder of the outer casing and a lid or seal can be removably attached to the outer casing to close in the adhesive fluid. The adhesive fluid is accessible when the lid or seal is removed. In an example, the lid or seal is bonded to the outer casing to close in the storage space or unit and retain the adhesive fluid therein. In other examples, the lid or seal may pressed fit to the outer casing or be pivotably attached to the outer casing. The terms storage space, storage unit, storage cavity, distal cavity, holding space, or storage holder can be used interchangeably to designate a space formed with the protective cap or attached to the protective cap and that can be closed in by a lid to seal in a fluid, solution, or object.

The protective cap of the present disclosure not only serves as a cover to shield the needle and envelope the catheter tube prior to use, the protective cap can incorporate a holding space to store a quantity of adhesive solution that can then be used to secure the catheter to the patient. Although an adhesive solution or fluid is disclosed as being stored in a storage space or cavity of the outer casing, it is also contemplated that other items can be stored in the storage cavity of the outer casing other than adhesive, such as tape, strings, stretch bands, ink, topical numbing cream, etc.

The adhesive stored in the storage cavity of the outer casing can be a topical skin adhesive or tissue adhesive glue that can polymerize in a short period of time following exposure to water or water containing substances like human tissue. The adhesive is configured for securing the catheter tube to the skin of the patient at the insertion point to anchor the catheter tube and prevent the catheter tube from unintended removal from the patient following successful venipuncture. The adhesive solution may also be used for securing the catheter hub to the patient. In an example, the topical skin adhesive is of the HISTOACRYL® adhesive type.

The outer casing of the protective cap can be made of a plastic material. In one example, the outer casing is made of a hard elastic transparent plastic such as polystyrene, polyethylene, polypropylene, polyethylene terephthalate (PET), polyethylene naphthylate (PEN), polymethylpentene (TP), acrylbutadienestyrene (ABS), and polycarbonate (PC). The plastic material should be medical grade if to be used in a clinical setting.

The outer casing can include a casing body, which can have a first section and a second section. The first section may alternatively be referred to as a distal section and the second section may alternatively be referred to as a proximal section located proximal of the distal section. The distal and proximal sections can be singularly formed or separately formed and subsequently joined together to form the casing body of the outer casing.

The distal section can include a generally elongated distal section body having a bore for receiving and covering the needle and the catheter tube to protect a user from accidental needle sticks prior to use and during packaging to prevent contamination of the needle and catheter tube, and to protect the plastic wrap from puncturing when the needle device is located inside the package. The distal section body can be sized and shaped to cover at least the length of the exposed portion of the needle and the catheter tube but can have other lengths to fit other sized needles or to fit a range of needle sizes.

The distal section body can be generally conical in cross-section but can embody other shapes, such as being cylindrical, tapered, oval, complex, irregular, or polygonal. The distal section body may be used by a user to grip and detach the protective cap from the needle device.

The distal section body may or can optionally include one or more viewing slots or vents. When more than one viewing slots are incorporated, the slots can be formed around a perimeter of the distal section body of the outer casing adjacent the distal end. The one or more viewing slots can allow the user to quickly identify whether the needle tip is present in the needle device. The viewing slots can also aid in venting during assembly of the protective cap to the needle device. There can be four elongated trapezoidal viewing slots equally spaced around the distal end of the distal section body.

The shape of the viewing slots is not limited to trapezoidal, and can be elliptical, rectangular, polygonal, irregular, or any other shape. Furthermore, the location of the one or more viewing slots is not limited to adjacent the distal end and can also be provided anywhere on the first and/or second portions of the outer casing including being randomly located on the cap and not equally spaced from one another.

The length of the distal section body can be longer than the length of the needle projecting out the catheter hub to ensure adequate clearance, spacing or gap with the needle tip. The length of the distal body portion can allow the protective cap to be used on different assemblies having different needle lengths. In other words, the protective cap can be a standard cap for a range of needle devices with different needle lengths. In some examples, the protective cap is configured to cap or house a needle without a catheter tube, such as an injection needle or an epidural needle. The solution stored in the protective cap can also be a topical skin adhesive used for wound closure applied to the insertion point after the needle is removed from the patient. The exact portion of the length of the needle and catheter tube that the distal section body covers can vary and can depend on various design factors.

In one embodiment, the diameter of the distal section body of the protective cap is generally constant along its longitudinal axis. In other embodiments, the diameter of the distal section body may taper away from or toward the proximal section from a distal end of the distal section body. That is, the distal section body of the outer casing can transition from a smaller diameter section at the distal end to an enlarged cross-sectional area at a proximal end, which is attached to the proximal section of the outer casing.

The distal section of the outer casing can have an elongated distal section body or elongated sleeve that transitions to a larger proximal section body of the proximal section. The second or proximal section can have a proximal section body, which can generally cover the catheter hub and optionally part of the needle hub. The shape of the proximal section body can closely match the shape of the portions of the catheter hub and the needle hub. The proximal section body of the outer casing can also serve as a grip for a user when detaching the protective cap from the needle device.

The proximal section body can have a proximal opening at a proximal end, which can be opened along a single plane. The proximal section can have an enlarged body, which can have a larger width, height, and/or diameter than the distal section body, for accommodating the catheter hub, needle hub, or both. In other examples, the proximal opening is not limited to a single plane. That is, part of the proximal opening can be at the proximal most end and can extend through part of the proximal section body, which is not formed with a full circumference. This irregular opening, instead of a single plane opening, can allow the protective cap to fit over irregular shaped hub bodies, such as ones with wings.

The protective cap can have a needle cavity for covering the catheter tube, if used with an over-the-needle device, and shielding the needle tip of a needle, which extends distally from the proximal opening through the proximal section body and into the distal section body to a distal end of the outer casing, which has a web or a barrier for forming part of the storage space for the adhesive solution, as further discussed below. The needle cavity can be sufficiently large to cover or at least partially surround the catheter hub, the catheter tube, the needle tip, and optionally the needle hub. In an example, the proximal section body surrounds the flange of the needle hub and a cut-out is provided at the proximal section to accommodate the wings.

A guiding lip having a slanted or tapered surface can be located at the proximal end at the proximal opening. The guiding lip can be formed for providing additional grip to a user for removing or attaching the protective cap from the needle device. The tapered surface of the guiding lip can help guide the cap over the needle device when installing the cap to the needle device.

The proximal opening can also extend distally along a side of the outer casing a certain distance to accommodate features of the needle device, as previously discussed. Said differently, a cutout can extend a certain distance from a proximal plane of the proximal opening along a side of the proximal section body and, if necessary, the distal section body of the outer casing.

The proximal opening can extend distally along an underside of the proximal section body and the distal section body to accommodate a pair of wings extending laterally out from the catheter hub of the needle device. The extension of the proximal opening along a side of the outer casing can also support operation of an engagement feature located on the protective cap for engaging a feature of the needle device. In an example, the engagement feature can be a catch, one or more slots, a detent, or a combination of features for positioning and holding a feature of the needle device in a manner such that the protective cap can be released from the needle device by force applied to one of the protective cap or the needle device.

The engagement feature can be slots located around an inner perimeter of the proximal section body adjacent the proximal end to engage the flange on the needle hub. Because the proximal opening can extend partially along a side of the outer casing, when a pulling force is applied, the proximal end can expand radially outwardly thereby moving the slots radially outwardly until the flange is no longer captured by the slots to enable disengagement of the protective cap from the needle device. The location of the engagement feature is not limited to near the proximal end of the outer casing, and may engage a feature of the catheter hub rather than the needle hub to secure the protective cap to the needle device prior to use. Other engagement mechanisms to secure the protective cap to the needle device are contemplated.

Referring again to the distal section of the outer casing, the distal section body has a distal opening at the distal end of the cap. The distal opening can be remote from the proximal opening of the protective cap. The distal opening can open up into a storage space or cavity. This feature is unique compared to prior art protective caps, which either do not have a distal opening or if one is included for venting, the size of the distal vent opening is relatively small and communicates with the needle cavity, meaning there is no web or barrier to isolate and separate a distal cavity from a proximal cavity.

In an example, a storage cavity for storing adhesive can extend proximally from the distal opening of the outer casing to the barrier or web formed inside the distal section body of the outer casing. In other words, starting from a distal most end of the protective cap, a distal cavity for storing is incorporated, which has a cavity bottom defined by a barrier or web.

The adhesive cavity can therefore be considered a distal cavity and the interior cavity or needle cavity for accommodating the needle can be considered a proximal cavity. The distal cavity and the proximal cavity can be separated from one another by the barrier or web. In an example, the distal cavity and the web are sized and shaped to accommodate a fluid and retain the fluid so that the fluid does not leak into the proximal cavity. Thus, the barrier can serve as an end wall for both the adhesive cavity and the needle cavity.

In an alternative embodiment, an adhesive holder or storage holder having a wall structure defining an adhesive cavity can be attached directly to the distal end of the outer casing of a conventional protective cap for forming a distal cavity for storing. The adhesive holder or storage holder can have a cup-like shape with a side wall and a bottom wall to form a barrier for storing, such as a fluid or a cream. In an example, the barrier separating the needle cavity from the adhesive cavity may be a bottom wall of the adhesive or storage holder and/or a distal end wall of the outer casing. In still other examples, the distal cavity may have a dividing wall to define two different distal cavity chambers. The two distal cavity chambers can store two different materials. In an example, one of the two distal cavity chambers can store an adhesive solution and the other distal cavity chamber can store an adhesive remover, alcohol, lotion, etc.

The distal end at the distal opening can serve as a rim of the adhesive cavity. The adhesive cavity or distal cavity can be sized and shaped for storing a quantity of adhesive solution, or other objects such as a topical cream or ink, and is structured to facilitate easy dispensing of the adhesive solution. The adhesive cavity or distal cavity can have a bowl-like or cup-like shape with a bottom wall substantially parallel to the rim and a frustoconical shaped sidewall extending between the rim and the bottom wall. In an example, the bottom wall may be angled with respect to the rim. In another example, a transition from the adhesive cavity or sidewall of the adhesive cavity to the rim can have a sharp edge, but can be a chamfered edge or a rounded edge. In still other examples, the rim can be angled such that a plane defined by the rim is angled relative to the lengthwise axis of the protective cap.

The shape of the rim, from an end view, can be generally circular. However, the rim can have other shapes to assist in pouring, such as an oval shape, a polygonal shape, or an irregular shape. In still yet another example, the shape of the rim can include a spout or pouring portion for easy pouring of the adhesive solution out of the cavity along the spout. In another example, more than one spout can extend from the rim of the adhesive cavity.

The distal end of the outer casing, which can be the rim of the adhesive cavity, can be flat or planar so that a lid or seal can attach at the distal or second opening of the protective cap. For example, the lid or seal can be attached to the rim to seal the solution inside the adhesive cavity or distal cavity. In another less preferred example, the rim may be non-planar.

The seal can attach to the distal end of the outer casing or the rim of the adhesive cavity by an adhesive, interference fit, a threaded engagement, ultrasonic welding or by other positive engagement means. The seal can be made of a similar material as the outer casing, a harder material, or a comparatively softer material. In an example, the seal can be made of a multi-laminate peelable layer having a metallic layer and a polymeric layer for bonding to the rim. In another example the seal can be made of single plastic material layer. In other examples, the seal can be made of a material that will not react with the adhesive stored in the adhesive cavity.

A peelable seal or lid described herein can comprise a sealing body and a tab extending from the sealing body, which can embody the distal end of protective caps described herein. The tab can extend or folded over along a side surface of the outer casing and can have any number of shapes, such as round, square, oval, etc. The sealing body can attach to the rim of the adhesive cavity. The sealing body can attach directly to the rim and can have an overhang that extends over the distal opening to cover the adhesive cavity and seal the adhesive solution inside the adhesive cavity. The lid or seal can be attached to the rim by an adhesive different than the adhesive in the adhesive cavity. The seal can instead be welded or heat sealed to the rim. The surface of the seal can have a texture, can have decorative features, and/or can have indicia with information.

The distal opening of the outer casing and the rim surrounding the outer perimeter of the adhesive cavity can be circular with a flat end. The shape of the rim and the distal opening are not limited and can be any shape including elliptical, polygonal, and irregular. As shown, the sealing body can also be circular to match the circular shape of the rim. The tab projects from a side of the sealing body and provides a grip for the user to remove the seal from the cap. That is, the tab of the sealing body can be configured for a user to grip and pull to detach the seal from the outer casing and more specifically to detach the seal from the rim surrounding the adhesive cavity to access the adhesive therein. The shape of the tab can be slightly smaller, equal to, or larger than the sealing body.

The sealing body and the tab can be made from a thin film material or a multi-laminate film. In an example, the thin film material can be an elastic plastic film material having a metallic film layer. The thickness of the film is not limited and can be any thickness provided it has sufficient strength to resist tearing to enable peeling the seal from the cap. In addition, the thickness of the lid or seal can vary along the sealing body. In another example, the seal may or may not have a tab attached to the sealing body so that the sealing body may be punctured by a tool to access the adhesive solution inside the adhesive cavity. To aid in dispensing the adhesive, the protective cap, the adhesive holder or the distal cavity, may be made of an elastic material to permit squeezing the walls surrounding the adhesive cavity to force the adhesive through the punctured sealing body.

The sealing body can have an inner surface for facing the adhesive cavity when attached to the rim and an outer surface opposite the inner surface exposed to the environment. The outer surface of the sealing body and the inner surface can have a rough texture or a smooth texture. The tab may similarly have an inner surface and an outer surface with a smooth texture or a rough texture. In an example, the inner surface can have a smooth texture to resist adherence of the adhesive to the inner surface, and both the inner and outer surfaces can have a rough texture to provide friction for a user when gripping and handling the tab to prevent the tab from slipping off the fingertips of the user.

A coating can also be applied to the inner surface to resist adherence of the adhesive solution to the inner surface. In an example, the coating can be a thin film of plastic applied to the inner surface to resist adherence and reacting with the adhesive.

In use and after the lid or seal is removed or separated from the rim, the protective cap can be tilted to cause the adhesive solution to flow from the adhesive cavity under gravity to dispense to the desired location on the patient, such as the insertion point to secure the catheter tube to the patient. In some examples, the protective cap is tilted to the side of the cap that has a spout or a notch.

A protective cap can include a pouring portion or spout incorporated at the rim or distal end of the outer casing. That is, the spout can have an extended portion that extends outwardly from an edge of the rim to define a flow channel to aid in pouring adhesive out from the adhesive cavity.

A raised lip can be provided at the rim having a surface that defines the boundary of the rim, including the spout. The rim can be circular with a projection breaking out from the circular portion to form the spout from which the adhesive can be poured. More specifically, the spout can project radially outwardly from the interior of the adhesive cavity to facilitate pouring of the adhesive out the adhesive cavity under gravity, after the seal attached to the rim is removed from the rim and the protective cap is tilted. The spout can project radially outwardly to permit directional flow of the adhesive out the adhesive cavity in the direction of the spout. With the spout, less tilting of the protective cap is required before the adhesive flows out the adhesive cavity compared to a similar cap without the spout.

A seal can attach to the rim of the adhesive or distal cavity to cover and maintain the adhesive in the adhesive cavity. The seal can comprise a sealing body and a tab projecting from the sealing body. In the illustrated embodiment, the sealing body can be circular but has a size that is sufficiently large to attach to the rim including the portion of the rim with the spout. Alternatively, the sealing body can be shaped to match the rim of the adhesive cavity, including an extended portion for covering the spout. The seal can be attached to the rim with the tab at a side of the spout away from the spout to provide a grip for the user.

In an example, an adhesive or storage holder is separately formed and subsequently attached to the distal end of the casing body of the protective cap. That is, the outer casing can include a casing body 319 and an adhesive holder fixed to the distal end of the casing body, such as by gluing, bonding, or welding, but not single injection molding. Alternatively, the adhesive holder can be unitary or singularly formed, such as by single injection molding, with the casing body.

In the separately formed adhesive holder or storage holder, the storage holder comprises a holder body having a rim surrounding a distal opening at a distal end. The adhesive cavity can extend proximally from the distal opening of the adhesive holder to either a bottom wall of the adhesive holder or to the distal end of the casing body if the holder body does not have a bottom wall. If the holder body has a bottom wall that defines the bottom of the distal cavity, then the casing body can also have a distal end wall at the distal end or the distal end can be without a distal wall.

The adhesive holder or storage holder can have a multi-point star shape and can include one or more pouring portions or spouts extending radially outwardly from the holder body along the entire length of the axis holder body. The six spouts can be spaced equidistantly apart around the adhesive holder to form a six-sided star shaped pattern. The spouts allow for the adhesive to be guided along the one or more spouts to the insertion point when the protective cap is tilted. One or more viewing slots or vents may also be provided through the casing body for venting or providing visual access to the needle tip. The sidewall of the holder body can taper inwardly so that the outer dimension at the rim reduces in the proximal direction towards the bottom of the holder body.

The lid for use with the adhesive holder of the present embodiment can comprise a cover removably attached to the rim of the adhesive holder and a handle extending from an outside surface of the cover away from the adhesive cavity. The handle can be cylindrical shaped with concave surfaces on the ends of the cylindrical shaped handle to provide gripping surfaces for a user to grasp and remove the lid from the casing body. The gripping surfaces may also have a rough texture to form a better grip. The handle may be raised by providing an upper stem between the handle and the cover. The lid can be detached from the rim by pulling, twisting, or shearing the lid from the rim.

A base can attach to a lower stem extending from the cover into the adhesive cavity from an inside surface of the cover. Viewed differently, the upper stem and the lower stem can be unitarily formed as a single stem and the cover co-molded or unitarily molded with the single stem. The stem can have a surface and can resemble a cylindrical shaft. The base can contact a bottom of the adhesive cavity or be spaced away from the bottom of the adhesive cavity when the cover is attached to the rim of the adhesive cavity. The diameter of the base is larger than a diameter of the lower stem so that adhesive can be supported on the lower stem and the base for direct application of the adhesive to the insertion point. Furthermore, upon removal of the lid from the outer casing, the base and the lower stem can act as a stirring device for mixing the adhesive solution prior to usage and application.

In a further example, a lid for use with the protective cap can comprise a cover, an upper stem, and a handle. The protective cap can comprise an outer casing having an adhesive cavity at a distal end and a lid having a cover attached to the distal end of the outer casing thereby sealing adhesive inside the adhesive cavity. The distal cavity can be singularly formed with the outer casing and can include a web to the divide the outer casing into a distal cavity and a proximal cavity. A handle can extend from the cover away from the adhesive cavity to form gripping surfaces for a user to detach the lid from the distal end of the outer casing thereby providing access to the adhesive in the adhesive cavity.

In a further example, a lid for use with the protective cap can include a lower stem or base extending into the adhesive cavity that is scallop shaped to enable scooping of the adhesive inside the adhesive cavity for direct application of the adhesive to the insertion point using a transfer means. Furthermore, upon removal of the lid from the outer casing, the scallop shaped lower stem or base can act as a stirring device for mixing the adhesive prior to usage and application.

Other features and aspects of the present disclosure are described further below.

BRIEF DESCRIPTION OF THE DRAWINGS

These and other features and advantages of the present devices, systems, and methods will become appreciated as the same becomes better understood with reference to the specification, claims and appended drawings wherein:

DETAILED DESCRIPTION

The detailed description set forth below in connection with the appended drawings is intended as a description of the presently preferred embodiments of protective caps for needle assemblies or needle devices provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
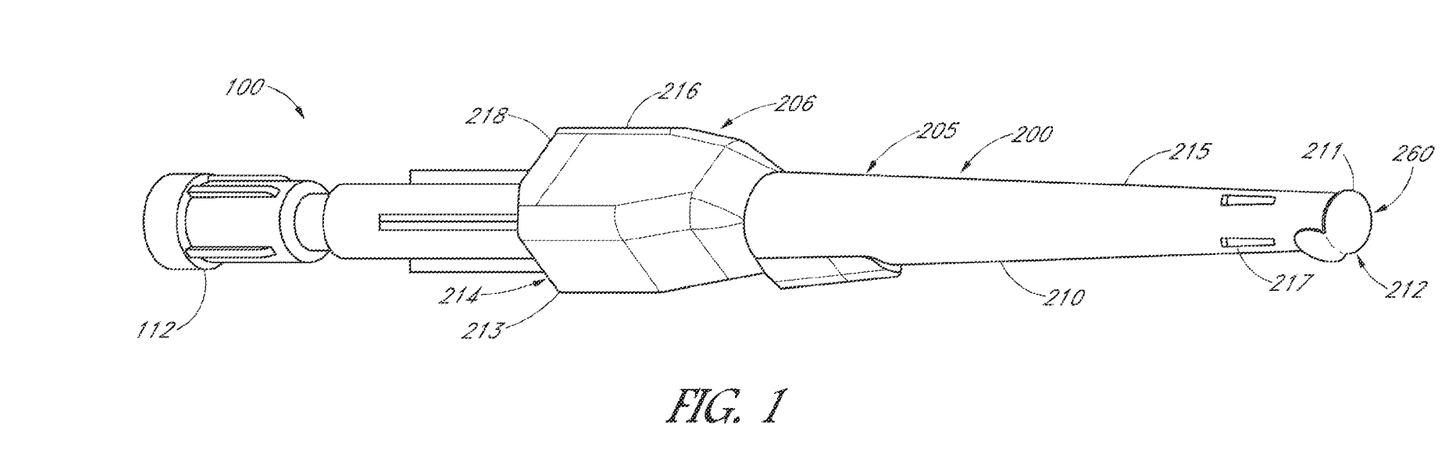
FIG. 1 is a perspective view of an embodiment of a needle assembly having a protective cap removably connected to a needle device.

FIG. 1 shows a perspective view of an IV catheter assembly or needle assembly 100, which comprises a needle cover or protective cap 200 removably connected to the catheter hub or needle hub of the catheter assembly. For example, the protective cap 200 can be positioned at least partly over the catheter hub 102 and covering the catheter tube 105 and the needle tip 108. The IV catheter assembly 100 may alternatively be referred to as an over-the needle catheter device or an IV catheter device, or a needle device. The needle device 100 may generally have a needle extending through a catheter tube with a needle tip extending out a distal end of the catheter tube. The catheter tube can extend distally from a catheter hub, and the needle extends distally from a needle hub. As used herein, the term proximal is understood to mean an end or side closer to the practitioner and the term distal is the opposite end or side. The protective cap 200 can shield the needle tip and cover the catheter tube prior to use, such as during packaging and storage of the assembly in a plastic wrap or a vacuum pack, to avoid accidental pricks or punctures prior to use.

Figure 2:
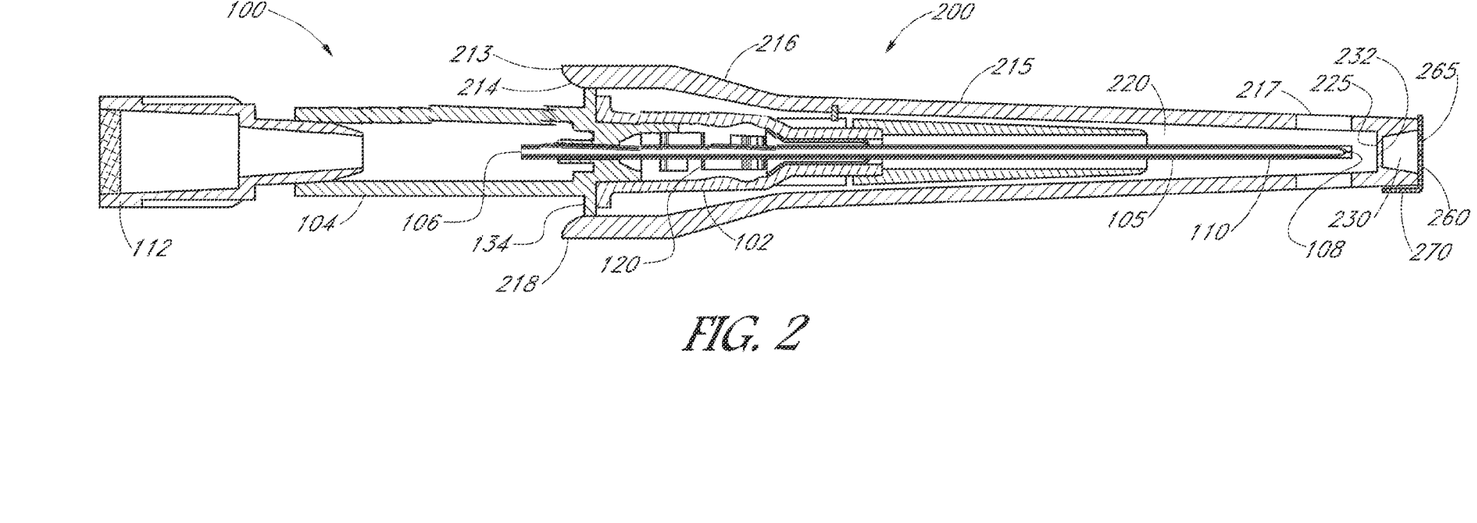
FIG. 2 is a schematic cross-sectional top view of the needle assembly of FIG. 1.
Figure 3:
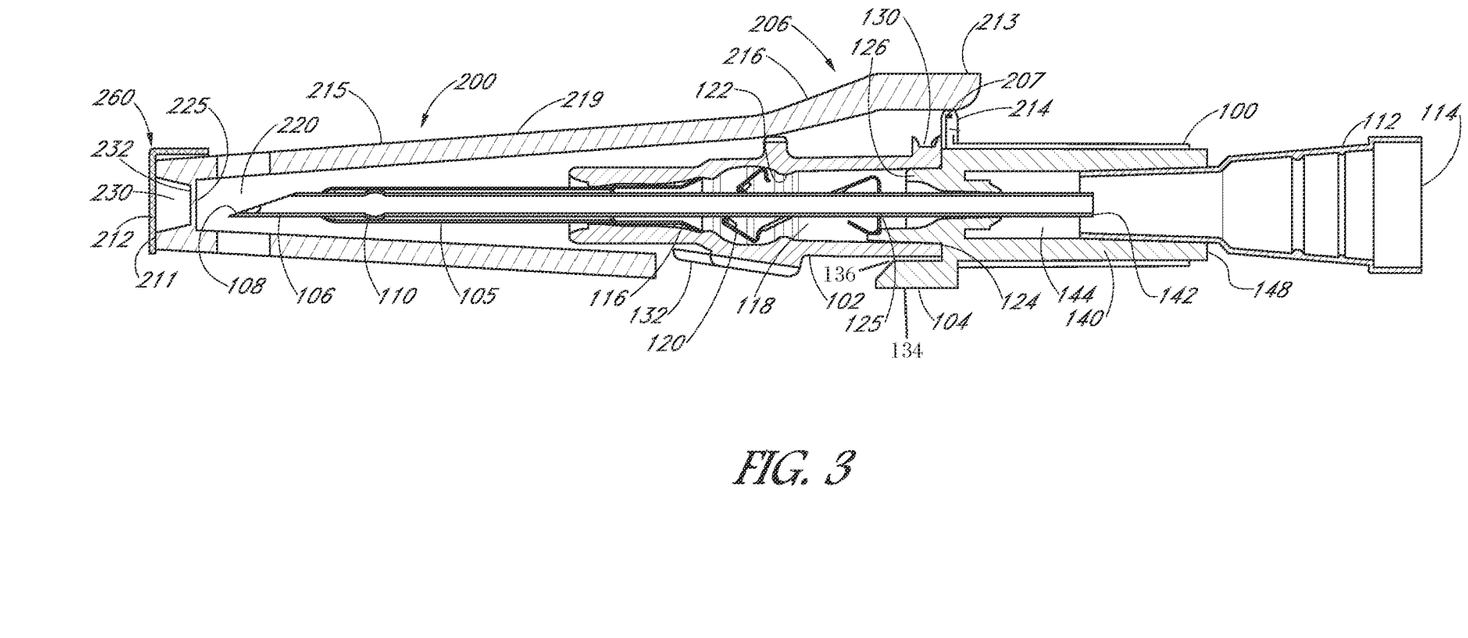
FIG. 3 is a schematic cross-sectional side view of the needle assembly of FIG. 1.

Referring now to FIGS. 2 and 3 and with continued reference to FIG. 1, the protective cap 200 can be firmly connected to the needle device 100 by frictional engagement and/or positive engagement, such as by detents. The needle device 100 can include a first hub or a catheter hub 102 having an over-the-needle catheter tube or tubing 105 attached thereto and a second hub or needle hub 104 having a needle 106 attached thereto. The catheter tube 105 can have a lumen or bore for receiving the needle and has a distal opening or distal end opening. The needle 106 has a needle tip 108 and can include a change in profile 110 located proximal of the tip 108 for use with a needle guard 120. The needle tip 108 extends distally of the distal end opening of the catheter tube 105 in the ready to use position with the change in profile 110, if incorporated, for use with a needle guard 120, located proximally of the distal tube opening. The change in profile 110 can be an enlarged section, such as a crimp, a bump, or a material build-up having a different profile than other diameter sections of the needle shaft.

The change in profile 110 can be used to interact with an opening 125 (FIG. 3) formed with a wall of a needle guard 120 during retraction of the needle 106, as further discussed below. A vent plug 112 is disposed at the proximal open end 148 of the second hub 104 and has a vent filter 114 at a proximal end thereof, which is conventional. As shown, the tube 105 is attached to the first hub 102 by a ferrule or metal bushing 116.

The needle guard 120 is optional and can be provided in the interior cavity 118 of the first hub 102 for covering the needle tip 108 in the protective position. When incorporated, the needle guard 120 can be one of the needle guards disclosed in U.S. Pat. No. 6,616,630, the contents of which are expressly incorporated herein by reference. In some examples, the needle guard 120 can be omitted. If so, the change in profile 110 can also be omitted. In still other examples, a needle guard can be included without also including a change in profile on the needle. In yet other examples, the needle guard 120 can be located in a third housing between the first hub and the second hub. An exemplary needle guard located in a third housing is disclosed in U.S. Pat. No. 8,597,249, the contents of which are expressly incorporated herein by reference.

In an example, the needle guard 120 can include a proximal wall and two arms extending distally of the proximal wall. The two arms can intersect one another in the ready to use position and in the protective position in which the needle guard covers the needle tip, and as viewed from a side. In some examples, the two arms of the needle guard 120 can extend in a distal direction without intersecting one another. Two distal walls, one on each arm, can be incorporated to block the needle tip. The two distal walls can be biased outwardly by the needle 106 in the ready to use position and disposed distally of an internal change in profile 122 (FIG. 3) inside the first hub 102 in the ready to use position.

The internal change in profile 122 can be a reduced diameter section located next to an inside diameter section of a larger dimension. Each distal wall on each arm can include a curved lip to eliminate having a blunt edge contacting the side of the needle to facilitate relative movement between the needle guard and the needle during retraction of the needle. When in the ready to use position, the dimension measured between the two joints at each arm, or elbows, at the intersection between each arm and its respective distal wall, is larger than the inside diameter of the internal change in profile 122 of the catheter hub, which prevents the needle guard 120 from moving proximally until the radial dimension at the two elbows of the needle guard 120 is reduced. Once the needle tip 108 moves proximally of the two distal walls, the two arms are allowed to move radially inward and one or both distal walls can close over the needle tip to block the needle tip in a protective position. At that point, the dimension between the two joints decreases and is smaller than the internal dimension of the internal change in profile 122, which then allows the needle guard 120 to move proximally and be removed from the catheter hub 102 with the needle 106.

The first hub 102 has a proximal opening 124 at a proximal end to receive a nose section 126 of the second hub 104 disposed therein. The proximal opening 124 can have a female Luer for receiving a male Luer tip, such as a syringe, an IV tubing adaptor, a Luer extension, etc. External threads 130 can be provided on the exterior surface at the proximal end of the first hub 102 for threaded engagement with a threaded collar of a male Luer tip. A pair of stabilizing wings 132 can extend radially of the first hub 102 to facilitate securement or anchoring of the first hub 102 to a patient following successful venipuncture. Optionally the wings 132 can be omitted. The first hub 102 can embody a standard IV catheter hub without a tubing port. In other examples, the first hub can include a tubing port. In still other examples, the first hub 102 can include a side fluid port, also known as a ported catheter.

The second hub 104 has a body 140 having an interior cavity 144 (FIG. 3) having the proximal end 142 of the needle 106 projecting there-into. The interior cavity 144 can function as a primary blood flashback chamber. The proximal opening 148 of the body 140 can have a female Luer for receiving a vent plug therein and the exterior can have threads or be without threads. In an example, the exterior of the body 140 of the second hub 104 is generally cylindrical and without threads. The first and second hubs can be made from plastic materials, such as by plastic injection. The body of second hub 104 may have some ergonomics grips or curvature, such as a flange extending outwardly from the body 140 near the distal end for use as leverage during venipuncture.

The first hub 102 can be removably secured to the second hub 104 having the nose section 126 of the second hub in the proximal opening 124 thereof. A flange or extension 134 can be provided on the second hub 104 and together with the nose section 126 define a gap 136 having part of the first hub located therein. Optionally the flange or extension 134 can be omitted and a stub or other surface mating features provided to limit the extent of insertion of the second hub 104 into the first hub 102. In an example, a rib or annular flange can also extend from the nose section 126 of the second hub 104 to limit the extent of insertion of the nose section 126 into the first hub 102.

The protective cap 200 can be assembled to the needle device by engaging or gripping a feature on the needle device 100, such as a feature on the catheter hub 102, the needle hub 104, or both, to secure the protective cap 200 to the needle device 100. The cap 200 prevents accidental contact with the needle tip and can prevent the needle hub 104 from detaching from the catheter hub 102 prior to use, such as from premature separation. In an example, the protective cap 200 can engage or grip the flange 134 or tab of the needle hub 104, the details of which are further discussed below. The protective cap 200 can be provided with the needle device 100 when the needle device is in its product packaging, such as peelable plastic shell or blister package.

When the needle device 100 is ready for use, the needle device and protective can first be removed from the product packaging then the protective cap 200 can be removed from the needle device 100 by pulling the protective cap 200 and the needle device 100 away from each other until a sufficient pulling force is reached to overcome the engagement between the protective cap 200 and the needle device 100. With the protective cap 200 separated from the needle device 100, the needle tip and the catheter tube are now exposed and ready for a user to access the vasculature of the patient. The point of insertion of the needle 106 and catheter tube 105 through the skin of the patient is known as an insertion point. After a successful venipuncture, the needle hub 104 can be retracted proximally away from the catheter hub 102 to remove the needle 106 from the patient with the catheter tube remaining implanted in the peripheral vein of the patient. Typically, a conventional protective cap is discarded once removed from the needle device 100. However, the protective cap 200 described herein can be retained and used after venipuncture, as detailed further below.

With further reference to FIGS. 1-3, the protective cap 200 can include three components, namely an outer casing 210, adhesive or fluid carried by the protective cap, and a seal or lid for closing in the fluid. In an example, the outer casing 210 can have a body 219 defining an interior space for accommodating the needle and a storage space or cavity for carrying the fluid. The adhesive fluid or solution can be carried in a cavity or holder 230 of the outer casing 210 and a lid or seal 260 can be removably attached to the outer casing 210 to close in the adhesive fluid. The adhesive fluid is accessible when the lid or seal is removed. In an example, the lid or seal 260 is bonded to the outer casing 210 to close in the storage space and retain the adhesive fluid therein. In other examples, the lid or seal 260 may pressed fit to the outer casing 210 or be pivotably attached to the outer casing 210.

The protective cap 200 of the present disclosure not only serves as a cover to shield the needle 106 and envelope the catheter tube 105 prior to use, the protective cap 200 can incorporate a holding space to store a quantity of adhesive solution that can then be used to secure the catheter to the patient. Although an adhesive solution or fluid is disclosed as being stored in a storage space or cavity 230 of the outer casing 210, it is also contemplated that other items can be stored in the storage cavity 230 of the outer casing 210 other than adhesive, such as tape, strings, stretch bands, ink, topical numbing cream, etc.

The adhesive stored in the cavity of the outer casing 210 can be a topical skin adhesive or tissue adhesive glue that can polymerize in a short period of time following exposure to water or water containing substances like human tissue. The adhesive is configured for securing the catheter tube 105 to the skin of the patient at the insertion point to anchor the catheter tube and prevent the catheter tube from unintended removal from the patient following successful venipuncture. The adhesive solution may also be used for securing the catheter hub to the patient. In an example, the topical skin adhesive is of the HISTOACRYL® adhesive type.

The outer casing 210 of the protective cap 200 can be made of a plastic material. In one example, the outer casing 210 is made of a hard elastic transparent plastic such as polystyrene, polyethylene, polypropylene, polyethylene terephthalate (PET), polyethylene naphthylate (PEN), polymethylpentene (TP), acrylbutadienestyrene (ABS), and polycarbonate (PC). The plastic material should be medical grade if to be used in a clinical setting.

The outer casing 210 includes a casing body 219, which can have a first section 205 and a second section 206. The first section 205 may alternatively be referred to as a distal section 205 and the second section 206 may alternatively be referred to as a proximal section 206 located proximal of the distal section 205. The distal and proximal sections 205, 206 can be singularly formed or separately formed and subsequently joined together to form the casing body 219 of the outer casing 210.

The distal section 205 can include a generally elongated distal section body 215 having a bore for receiving and covering the needle 106 and the catheter tube 105 to protect a user from accidental needle sticks prior to use and during packaging to prevent contamination of the needle 106 and catheter tube 105, and to protect the plastic wrap from puncturing when the needle device 100 is located inside the package. The distal section body 215 can be sized and shaped to cover at least the length of the exposed portion of the needle 106 and the catheter tube 105 but can have other lengths to fit other sized needles or to fit a range of needle sizes. As shown, the distal section body 215 is generally conical in cross-section but can embody other shapes, such as being cylindrical, tapered, oval, complex, irregular, or polygonal. The distal section body 215 may be used by a user to grip and detach the protective cap 200 from the needle device 100.

The distal section body 215 may or can optionally include one or more viewing slots or vents 217. When more than one viewing slots 217 are incorporated, the slots can be formed around a perimeter of the distal section body 215 of the outer casing 210 adjacent the distal end 211. The one or more viewing slots 217 can allow the user to quickly identify whether the needle tip 108 is present in the needle device 100. The viewing slots 217 can also aid in venting during assembly of the protective cap 200 to the needle device 100. As shown, there are four elongated trapezoidal viewing slots 217 equally spaced around the distal end 211 of the distal section body 215. The shape of the viewing slots 217 is not limited to trapezoidal, and can be elliptical, rectangular, polygonal, irregular, or any other shape. Furthermore, the location of the one or more viewing slots 217 is not limited to adjacent the distal end 211 and can also be provided anywhere on the first and/or second portions 205, 206 of the outer casing 210, including being randomly located on the cap and not equally spaced from one another.

The length of the distal section body 215 can be longer than the length of the needle 106 projecting out the catheter hub 102 to ensure adequate clearance, spacing or gap with the needle tip 108. The length of the distal body portion 215 can allow the protective cap 200 to be used on different assemblies having different needle lengths. In other words, the protective cap 200 can be a standard cap for a range of needle devices. In some examples, the protective cap 200 is configured to cap or house a needle without a catheter tube, such as an injection needle or an epidural needle. The adhesive stored in the protective cap 200 can also be a topical skin adhesive used for wound closure applied to the insertion point after the needle 106 is removed from the patient. The exact portion of the length of the needle 106 and catheter tube 105 that the distal section body 215 covers can vary and can depend on various design factors.

In one embodiment, the diameter of the distal section body 215 is generally constant along its longitudinal axis. In other embodiments, the diameter of the distal section body 215 may taper away from or toward the proximal section 216 from a distal end 211 of the distal section body 215. That is, the distal section body 215 of the outer casing 210 can transition from a smaller diameter section at the distal end 211 to an enlarged cross-sectional area at a proximal end, which is attached to the proximal section 216 of the outer casing 210, as further discussed below. As shown, the distal section 205 of the outer casing 210 has an elongated distal section body 215 or elongated sleeve that transitions to a larger proximal section body 216 of the proximal section 206. The second or proximal section 206 has a proximal section body 216, which generally covers the catheter hub 102 and optionally part of the needle hub 104. The shape of the proximal section body 216 can closely match the shape of the portions of the catheter hub 102 and the needle hub 104. The proximal section body 216 of the outer casing 210 can also serve as a grip for a user when detaching the protective cap 200 from the needle device 100.

The proximal section body 216 has a proximal opening 214 at a proximal end 213, which can be opened along a single plane as shown in FIG. 2. The proximal section can have an enlarged body, which can have a larger width, height, and/or diameter than the distal section body 215, for accommodating the catheter hub, needle hub, or both. In other examples, the proximal opening is not limited to a single plane. That is, part of the proximal opening 214 can be at the proximal most end and can extend through part of the proximal section body 216, which is not formed with a full circumference, as shown in FIG. 3. This irregular opening, instead of a single plane opening, can allow the protective cap to fit over irregular shaped hub bodies, which as ones with wings.

The protective cap has a needle cavity 220 for covering the catheter tube 105 and shielding the needle tip 108, which extends distally from the proximal opening 214 through the proximal section body 216 and into the distal section body 215 to a distal end of the outer casing 210, which has a web or a barrier 225 for forming part of the storage space for the adhesive solution, as further discussed below. The needle cavity 220 can be sufficiently large to cover or at least partially surround the catheter hub 102, the catheter tube 105, the needle tip 108, and optionally the needle hub 104. In an example, the proximal section body 216 surrounds the flange 134 of the needle hub 104 and a cut-out is provided at the proximal section 216 to accommodate the wings 132.

A guiding lip 218 having a slanted or tapered surface is located at the proximal end 213 at the proximal opening 214. The guiding lip 218 can be formed for providing additional grip to a user for removing or attaching the protective cap 200 from the needle device 100. The tapered surface of the guiding lip 218 can help guide the cap over the needle device when installing the cap to the needle device.

The proximal opening 214 can also extend distally along a side of the outer casing 210 a certain distance to accommodate features of the needle device 100, as previously discussed. Said differently, a cutout can extend a certain distance from a proximal plane of the proximal opening 214 along a side of the proximal section body 216 and, if necessary, the distal section body 215 of the outer casing 210. As shown, the proximal opening 214 extends distally along an underside of the proximal section body 216 and the distal section body 215 to accommodate a pair of wings 132 extending laterally out from the catheter hub 102 of the needle device 100. The extension of the proximal opening 214 along a side of the outer casing 210 can also support operation of an engagement feature 207 located on the protective cap 200 for engaging a feature of the needle device 100. In an example, the engagement feature 207 can be a catch, one or more slots, a detent, or a combination of features for positioning and holding a feature of the needle device 100 in a manner such that the protective cap 200 can be released from the needle device 100 by force applied to one of the protective cap 200 or the needle device 100. As shown, the engagement feature 207 are slots located around an inner perimeter of the proximal section body 216 adjacent the proximal end 213 to engage the flange 134 on the needle hub 104. Because the proximal opening 214 can extend partially along a side of the outer casing 100, when a pulling force is applied, the proximal end can expand radially outwardly thereby moving the slots radially outwardly until the flange 134 is no longer captured by the slots to enable disengagement of the protective cap 200 from the needle device 100. The location of the engagement feature 207 is not limited to near the proximal end 213 of the outer casing 210, and may engage a feature of the catheter hub 102 rather than the needle hub 104 to secure the protective cap 200 to the needle device 100 prior to use.

Referring again to the distal section 205 of the outer casing 210, the distal section body 215 has a distal opening 212 at the distal end 211 of the cap. The distal opening 212 can be remote from the proximal opening of the protective cap. This feature is unique compared to prior art protective caps, which either do not have a distal opening or if one is included for venting, the size of the distal vent opening is relatively small and communicates with the needle cavity 220, meaning there is no web or barrier to isolate and separate a distal cavity from a proximal cavity. In an example, a cavity 230 for storing adhesive can extend proximally from the distal opening 212 of the outer casing 210 to the barrier or web 225 formed inside the distal section body 215 of the outer casing 210. In other words, starting from a distal most end of the protective cap, a distal cavity 230 for storing is incorporated, which has a cavity bottom defined by a barrier or web 225.

The adhesive cavity 230 can therefore be considered a distal cavity and the interior cavity or needle cavity 220 for accommodating the needle can be considered a proximal cavity. The distal cavity 230 and the proximal cavity 220 are separated from one another by the barrier or web 225. In an example, the distal cavity and the web are sized and shaped to accommodate a fluid and retain the fluid so that the fluid does not leak into the proximal cavity. Thus, the barrier 225 can serve as an end wall for both the adhesive cavity 230 and the needle cavity 220. In an alternative embodiment, an adhesive holder or storage holder 235 having a wall structure defining an adhesive cavity 230 can be attached directly to the distal end of the outer casing of a conventional protective cap for forming a distal cavity for storing. The adhesive holder can have a cup-like shape with a side wall and a bottom wall to form a barrier for storing, such as a fluid or a cream. In this example, the barrier 225 separating the needle cavity 220 from the adhesive cavity 230 may be a bottom wall of the adhesive or storage holder 235 and/or a distal end wall of the outer casing 210, as will be discussed later with reference to FIGS. 8-11. In still other examples, the distal cavity 230 may have a dividing wall to define two different distal cavity chambers. The two distal cavity chambers can store two different materials. In an example, one of the two distal cavity chambers can store adhesive solution and the other distal cavity chamber can store adhesive remover, alcohol, lotion, etc.

The distal end 211 at the distal opening 212 can serve as a rim of the adhesive cavity 230. The adhesive cavity or distal cavity 230 can be sized and shaped for storing a quantity of adhesive solution, or other objects such as a topical cream or ink, and is structured to facilitate easy dispensing of the adhesive solution. As shown, the adhesive cavity or distal cavity 230 has a bowl-like or cup-like shape with a bottom wall 232 substantially parallel to the rim 211 and a frustoconical shaped sidewall extending between the rim 211 and the bottom wall 232. In an example, the bottom wall 232 may be angled with respect to the rim 211. In another example, a transition from the adhesive cavity 230 or sidewall of the adhesive cavity 230 to the rim 211 is shown as a sharp edge, but can be a chamfered edge or a rounded edge. In still other examples, the rim 211 can be angled such that a plane defined by the rim is angled relative to the lengthwise axis of the protective cap.

The shape of the rim 211, from an end view, can be generally circular. However, the rim 211 can have other shapes to assist in pouring, such as an oval shape, a polygonal shape, or an irregular shape. In still yet another example, the shape of the rim 211 can include a spout or pouring portion 275 as discussed below with reference to FIGS. 6 and 7, for easy pouring of the adhesive solution out of the cavity along the spout 275. In another example, more than one spout 275 can extend from the rim 211 of the adhesive cavity 230 as discussed below with reference to FIGS. 8-10.

The distal end 211 of the outer casing 210, which is also the rim 211 of the adhesive cavity 230, can be flat or planar so that a lid or seal 260 can be attached at the distal or second opening of the protective cap. For example, the lid or seal 260 can be attached to the rim 211 to seal the solution inside the adhesive cavity or distal cavity 230. In another less preferred example, the rim 211 may be non-planar. The seal 260 can attach to the distal end of the outer casing 210 or the rim 211 of the adhesive cavity 230 by an adhesive, interference fit, a threaded engagement, ultrasonic welding or by other positive engagement means. The seal 260 can be made of a similar material as the outer casing 210, a harder material, or a comparatively softer material. In an example, the seal 260 can be made of a multi-laminate peelable layer having a metallic layer and a polymeric layer for bonding to the rim. In another example the seal can be made of single plastic material layer. In other examples, the seal 260 can be made of a material that will not react with the adhesive stored in the adhesive cavity 230.

Figure 4:
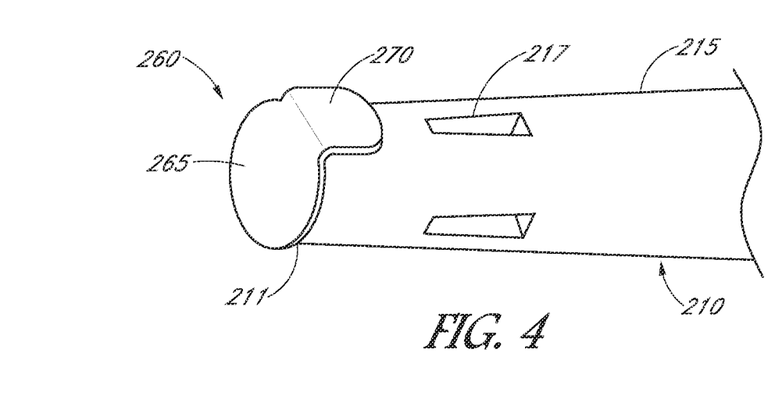
FIG. 4 is an enlarged view of the protective cap in FIG. 1, showing one embodiment of the protective cap.
Figure 5:
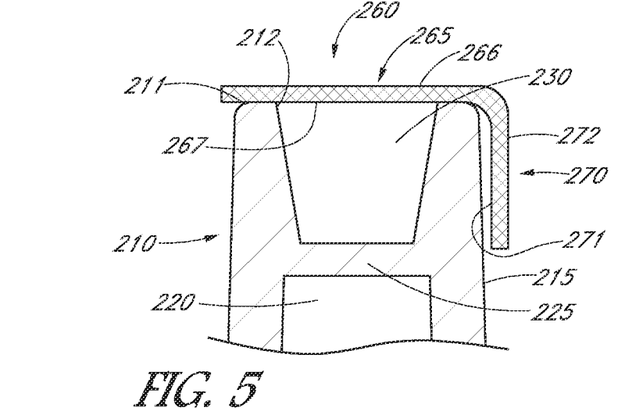
FIG. 5 is a partial schematic cross-sectional view the protective cap of FIG. 4.

Referring now to FIGS. 4 and 5, a peelable seal or lid 260 is shown comprising a sealing body 265 and a tab 270 extending from the sealing body 265, which can embody the distal end of the protective cap of anyone of FIGS. 1-3. The tab 270 can extend or folded over along a side surface of the outer casing 210 and can have any number of shapes, such as round, square, oval, etc. The sealing body 265 is shown attached to the rim 211 of the adhesive cavity 230. The sealing body 265 is attached directly to the rim 211 and has an overhang that extends over the distal opening 212 to cover the adhesive cavity 230 and seal the adhesive solution inside the adhesive cavity 230. The lid or seal 260 can be attached to the rim 211 by an adhesive different than the adhesive in the adhesive cavity. The seal can instead be welded or heat sealed to the rim 211. The surface of the seal 260 can have a texture, can have decorative features, and/or can have indicia with information.

As shown, the distal opening 212 of the outer casing 210 and the rim 211 surrounding the outer perimeter of the adhesive cavity 230 are circular with a flat end. The shape of the rim 211 and the distal opening 212 are not limited and can be any shape including elliptical, polygonal, and irregular. As shown, the sealing body 265 is also circular to match the circular shape of the rim 211. The tab 270 projects from a side of the sealing body 265 and provides a grip for the user to remove the seal from the cap. That is, the tab 270 of the sealing body 265 is configured for a user to grip and pull to detach the seal 260 from the outer casing and more specifically to detach the seal from the rim 211 surrounding the adhesive cavity 230 to access the adhesive therein. The shape of the tab 270 can be slightly smaller, equal to, or larger than the sealing body 265.

The sealing body 265 and the tab 270 can be made from a thin film material or a multi-laminate film. In an example, the thin film material can be an elastic plastic film material having a metallic film layer. The thickness of the film is not limited and can be any thickness provided it has sufficient strength to resist tearing to enable peeling the seal from the cap. In addition, the thickness of the lid or seal 260 can vary along the sealing body 265. In another example, the seal 260 may or may not have a tab 270 attached to the sealing body 265 so that the sealing body 265 may be punctured by a tool to access the adhesive solution inside the adhesive cavity 230. To aid in dispensing the adhesive, the protective cap 210, the adhesive holder or the distal cavity, may be made of an elastic material to permit squeezing the walls surrounding the adhesive cavity 230 to force the adhesive through the punctured sealing body 265.

The sealing body 265 can have an inner surface 267 for facing the adhesive cavity 230 when attached to the rim 211 and an outer surface 266 opposite the inner surface 267 exposed to the environment. The outer surface 266 of the sealing body 265 and the inner surface 267 can have a rough texture or a smooth texture. The tab 270 may similarly have an inner surface 271 and an outer surface 272 with a smooth texture or a rough texture. In an example, the inner surface 267 can have a smooth texture to resist adherence of the adhesive to the inner surface 267, and both the inner and outer surfaces 271, 272 can have a rough texture to provide friction for a user when gripping and handling the tab 270 to prevent the tab 270 from slipping off the fingertips of the user. A coating can also be applied to the inner surface 267 to resist adherence of the adhesive solution to the inner surface. In an example, the coating can be a thin film of plastic applied to the inner surface 267 to resist adherence and reacting with the adhesive.

In use and after the lid or seal 260 is removed from the rim 211, the protective cap 210 can be tilted to cause the adhesive solution to flow from the adhesive cavity 230 under gravity to dispense to the desired location on the patient, such as the insertion point to secure the catheter tube 105 to the patient. In some examples, the protective cap 210 is tilted to the side of the cap that has a spout or a notch.

Figure 6:
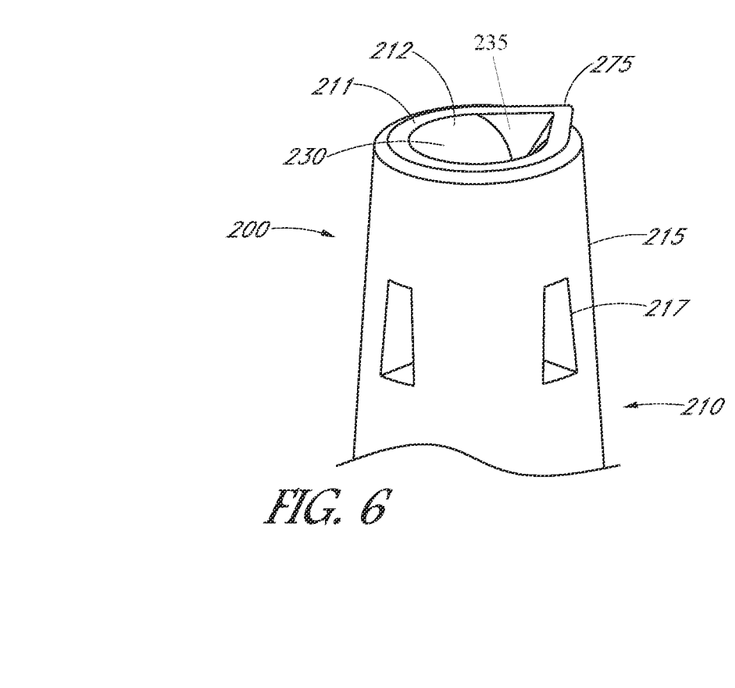
FIG. 6 is partial perspective view of another embodiment of the protective cap, the protective cap including a seal and an outer casing having a spout for easy pouring.
Figure 7:
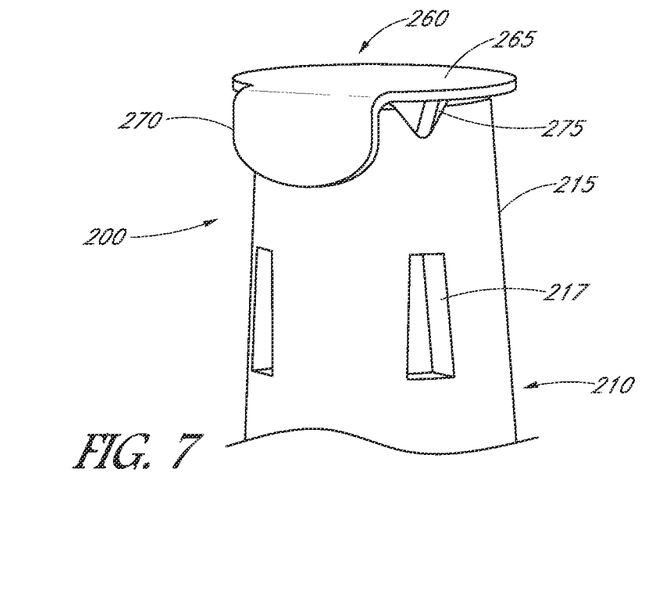
FIG. 7 is a partial perspective view of the protective cap of FIG. 6, shown without the seal attached to the outer casing.

FIGS. 6 and 7 illustrate another embodiment of a protective cap 200. The protective cap of FIGS. 6 and 7 is similar to the protective cap 200 of FIGS. 4 and 5 and can be used with a needle device as described for FIGS. 4 and 5 except that a pouring portion or spout 275 is incorporated at the rim 211 or distal end of the outer casing 210. That is, the spout 275 has an extended portion that extends outwardly from an edge of the rim to define a flow channel to aid in pouring adhesive out from the adhesive cavity 230. A raised lip can be provided at the rim having a surface that defines the boundary of the rim, including the spout. As shown the rim 211 is circular with a projection breaking out from the circular portion to form the spout 275 from which the adhesive can be poured. More specifically, the spout 275 projects radially outwardly from the interior of the adhesive cavity 230 to facilitate pouring of the adhesive out the adhesive cavity 230 under gravity, after the seal 260 attached to the rim is removed from the rim and the protective cap 200 is tilted. The spout 275 projects radially outwardly to permit directional flow of the adhesive out the adhesive cavity in the direction of the spout 275. With the spout 275, less tilting of the protective cap 200 is required before the adhesive flows out the adhesive cavity 230 compared to a similar cap without the spout.

The lid or seal 260 of FIGS. 6 and 7 is also similar to the seal 260 of FIGS. 4 and 5. The seal 260 is attached to the rim 211 of the adhesive cavity 230 to cover and maintain the adhesive in the adhesive cavity 230. The seal 260 comprises a sealing body 265 and a tab 270 projecting from the sealing body 265. In the illustrated embodiment, the sealing body 265 is circular but has a size that is sufficiently large to attach to the rim 211 including the portion of the rim 211 with the spout 275. Alternatively, the sealing body 265 can be shaped to match the rim 211 of the adhesive cavity 230, including an extended portion for covering the spout 275. The seal 260 can be attached to the rim 211 with the tab 270 at a side of the spout 275 away from the spout 275 to provide a grip for the user, as shown in FIG. 7.

FIGS. 8-11 illustrate another embodiment of a protective cap 300. The protective cap 300 includes an outer casing 310 having a casing body 319 and a seal or lid 360. The outer casing 310 is similar to the outer casings 210 of FIGS. 4-5 and 6-7 and can be used with a needle device as described except that the adhesive cavity 330 for storing adhesive solution is formed in an adhesive or storage holder 335 that is separately formed and subsequently attached to the distal end 311 of the casing body 319. That is, the outer casing 310 includes a casing body 319 and an adhesive holder 335 fixed to the distal end 311 of the casing body 319. Alternatively, the adhesive holder 335 can be unitary or singularly formed with the casing body 319, such as by injection molding.

In the embodiment shown, the adhesive or storage holder 335 comprises holder body 334 having a rim 336 surrounding a distal opening 332 at a distal end 311. The adhesive cavity 330 can extend proximally from the distal opening 332 of the adhesive holder 335 to either a bottom wall of the adhesive holder 335 or to the distal end 311 of the casing body 319 if the holder body 334 does not have a bottom wall. If the holder body 334 has a bottom wall that defines the bottom of the distal cavity 330, then the casing body 319 can also have a distal end wall at the distal end 311 or the distal end can be without a distal wall. The adhesive holder or storage holder 335 can have a multi-point star shape and can include one or more pouring portions or spouts 333 extending radially outwardly from the holder body 334 along the entire length of the holder body 334. As shown, six spouts 333 are spaced equidistantly apart around the adhesive holder 335 to form a six-sided star shaped pattern. As discussed above for the spout 275 of FIGS. 6 and 7, the spouts 333 allow for the adhesive to be guided along the one or more spouts 333 to the insertion point when the protective cap is tilted. One or more viewing slots 317 similar to the one or more viewing slots 217 of FIGS. 4 and 5 may also be provided through the casing body 319 for venting or providing visual access to the needle tip 108. The sidewall of the holder body 334 can taper inwardly so that the outer dimension at the rim 336 reduces in the proximal direction towards the bottom of the holder body 334.

The lid 360 for use with the adhesive holder 335 of the present embodiment can comprise a cover 364 removably attached to the rim 336 of the adhesive holder 335 and a handle 362 extending from an outside surface of the cover 364 away from the adhesive cavity 330. The handle 362 can be cylindrical shaped with concave surfaces on the ends of the cylindrical shaped handle to provide gripping surfaces for a user to grasp and remove the lid 360 from the casing body 319. The gripping surfaces may also have a rough texture to form a better grip. The handle 362 may be raised by providing an upper stem 363 between the handle 362 and the cover 364. The lid 360 can be detached from the rim 336 by pulling, twisting, or shearing the lid 360 from the rim 336.

Figures 8, 9, 10, 11:
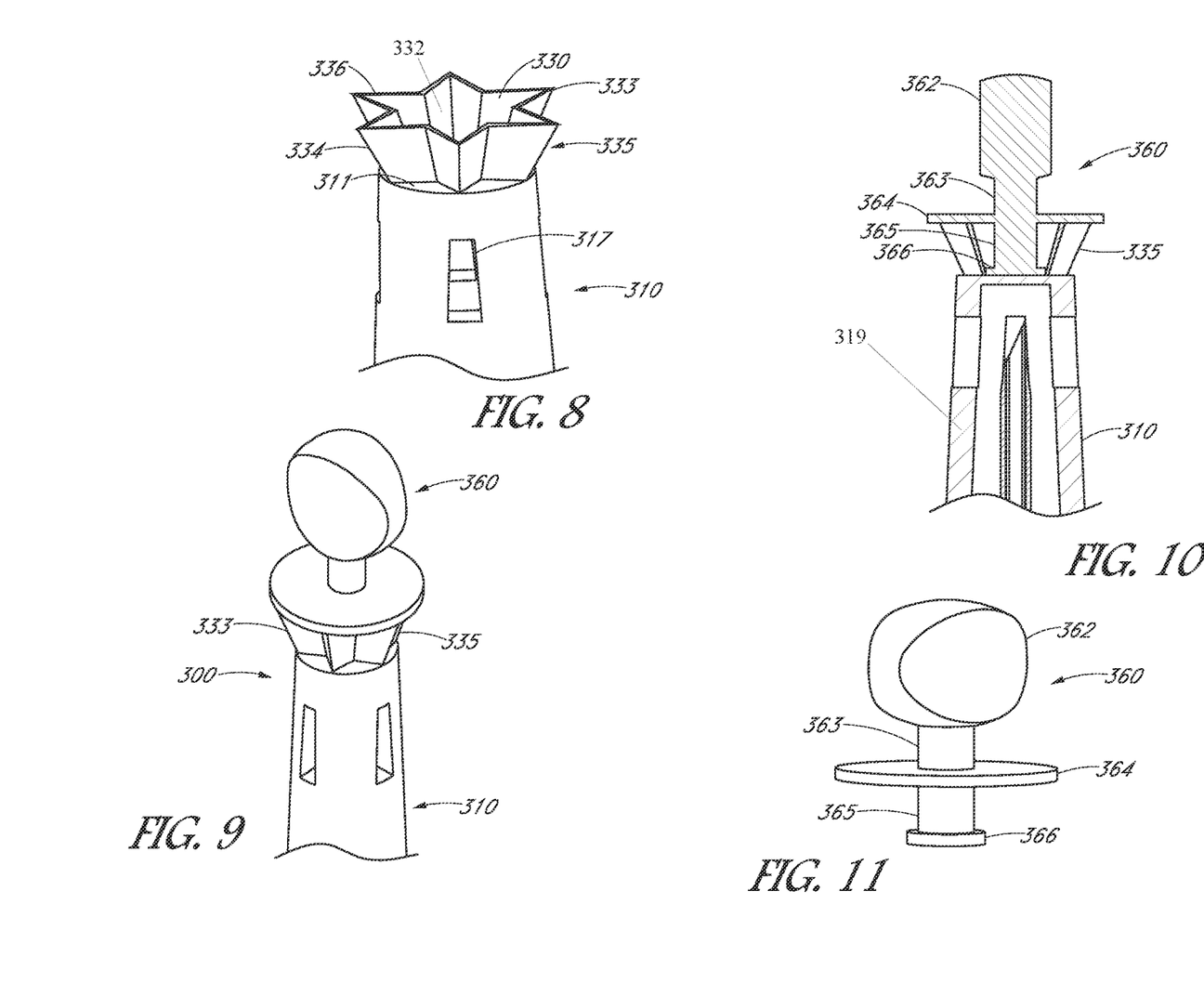
FIG. 8 is a partial perspective view of yet another embodiment of the protective cap of FIG. 1, the protective cap including a seal and an external cavity attached to a distal end of an outer casing.
FIG. 9 is a partial schematic cross-sectional view of the protective cap of FIG. 8.
FIG. 10 is a partial perspective view of the outer casing of the protective cap of FIG. 8.
FIG. 11 is a perspective view of the seal of the protective cap of FIG. 8.

A base 366 is attached to a lower stem 365 extending from the cover 364 into the adhesive cavity 330 from an inside surface of the cover 364. Viewed differently, the upper stem 363 and the lower stem 365 can be unitarily formed as a single stem and the cover 364 co-molded or unitarily molded with the single stem. The base 366 can contact a bottom of the adhesive cavity 330 or be spaced away from the bottom of the adhesive cavity 330 when the cover 334 is attached to the rim 336 of the adhesive cavity 330. The diameter of the base 366 is larger than a diameter of the lower stem 365 so that adhesive can be supported on the lower stem 365 and the base 366 for direct application of the adhesive to the insertion point. Furthermore, upon removal of the lid 360 from the outer casing 310, the base 366 and the lower stem 363 can act as a stirring device for mixing the adhesive solution prior to usage and application.

Figure 12:
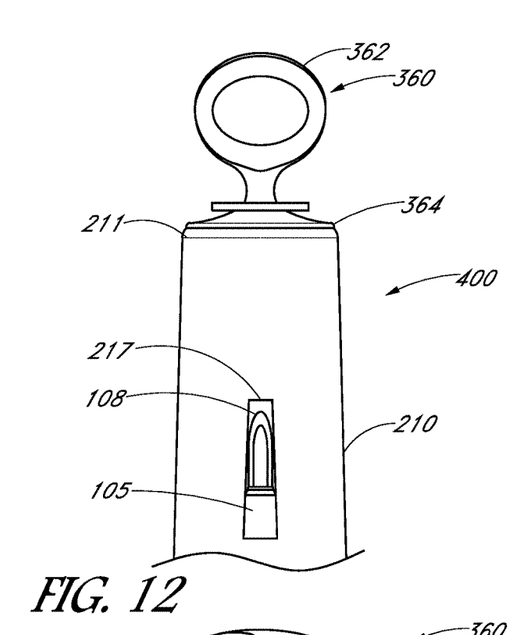
FIG. 12 is a partial perspective view of another embodiment of a needle assembly, the needle assembly including a protective cap including a seal attached to an outer casing.
Figure 13:
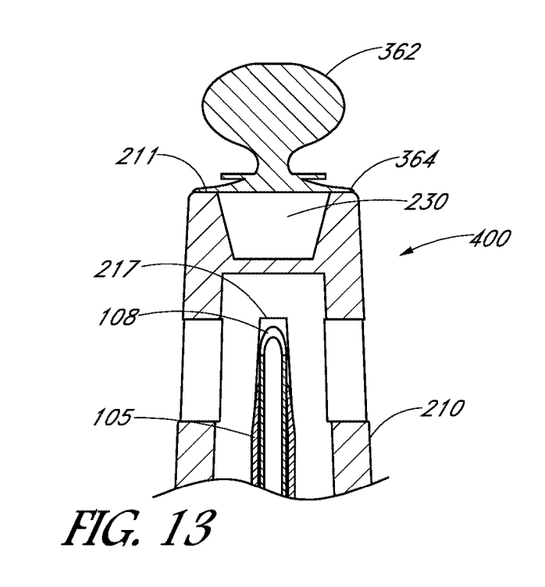
FIG. 13 is a partial schematic cross-sectional view of the needle assembly of FIG. 12.

FIGS. 12 and 13 illustrate another embodiment of a protective cap 400. The protective cap 400 comprises an outer casing 210 similar to the outer casings 210 of FIGS. 4-7, and a lid 360 similar to the lid 360 of FIGS. 9-11 without the base 366 and lower stem 365. The present protective cap 400 can be used with a needle device as described with reference to FIGS. 4-7 and 9-11.

The lid 360 can comprise a cover 364, an upper stem 363, and a handle 362. The protective cap 400 can comprise an outer casing 210 having an adhesive cavity 230 at a distal end 211 and a lid 360 having a cover 364 attached to the distal end 211 of the outer casing 210 thereby sealing adhesive inside the adhesive cavity 230. The distal cavity 230 can be singularly formed with the outer casing 210 and can include a web to the divide the outer casing into a distal cavity and a proximal cavity. A handle 362 extends from the cover 364 away from the adhesive cavity 230 to form gripping surfaces for a user to detach the lid 360 from the distal end 211 of the outer casing 210 thereby providing access to the adhesive in the adhesive cavity 230.

Figure 14:
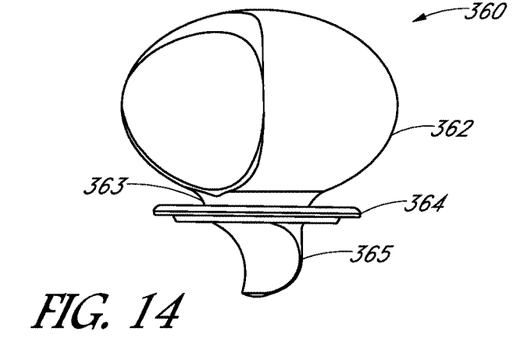
FIG. 14 is partial schematic cross-sectional view of another embodiment of a needle assembly, the needle assembly including a protective cap, the protective cap including a seal having a scalloped end.
Figure 15:
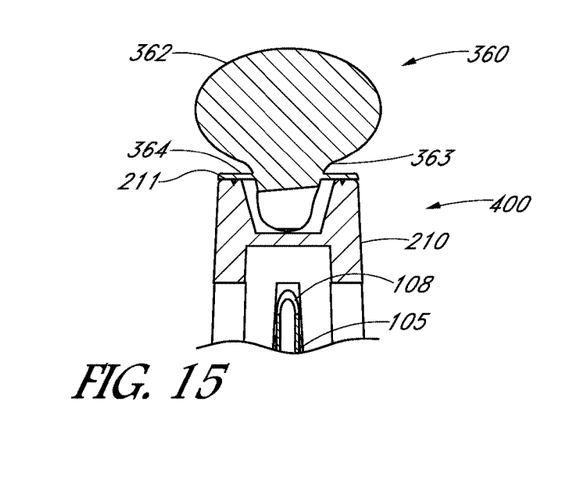
FIG. 15 is a perspective view of the seal of FIG. 14.

FIGS. 14 and 15 illustrate yet another embodiment of a protective cap 400. The protective cap 400 comprises an outer casing 210 similar to the outer casing 210 of FIGS. 4-7, and a lid 360 similar to the lid 360 of FIGS. 9-11 except that the lower stem 365 or base 366 extending into the adhesive cavity 230 is scallop shaped to enable scooping of the adhesive inside the adhesive cavity 230 for direct application of the adhesive to the insertion point using a transfer means. Furthermore, upon removal of the lid 360 from the outer casing 210, the scallop shaped lower stem 365 or base 366 can act as a stirring device for mixing the adhesive prior to usage and application. The present protective cap 400 can be used with a needle device as described with reference to FIGS. 4-7 and 9-11.

Methods of making and using needle assemblies or devices and components thereof, including protective caps with proximal and distal cavities, are within the scope of the present invention.

Although limited embodiments of the needle devices, protective caps, and their components have been specifically described and illustrated herein, many modifications and variations will be apparent to those skilled in the art. For example, the various protective caps may incorporate other attachments, etc. Furthermore, it is understood and contemplated that features specifically discussed for one protective cap embodiment may be adopted for inclusion with another protective cap embodiment, provided the functions are compatible. For example, the lid or seal of one protective cap may be used in another embodiment shown with a different outer casing. This allows the lids or seals to be used interchangeably for different outer casings. Accordingly, it is to be understood that the needle devices, protective caps, and their components constructed according to principles of the disclosed device, system, and method may be embodied other than as specifically described herein. The disclosure is also defined in the following claims.

What is claimed is:

1. A needle assembly, comprising:
   a catheter hub, a catheter tube extending distally from the catheter hub and a needle hub having a needle having a needle tip extending out a distal end of the catheter tube;
   a unitary formed protective cap positioned at least partly over the catheter hub and covering the catheter tube and the needle tip, the protective cap comprising:
      a casing having a casing wall defining a body and the casing wall comprising an exterior surface and an interior surface;
      a first opening at a proximal end of the body, a proximal cavity defined by the interior surface of the casing wall at the first opening having the needle tip and the catheter tube located therein, a second opening of the body remote from the first opening, a distal cavity defined by the interior surface of the casing wall at the second opening, a continuous barrier formed with the interior surface of the casing wall to separate the distal cavity having a first size from the proximal cavity having a second size, and a rim at the second opening; and
   a lid removably attached at the second opening to seal in a solution inside the distal cavity;
   wherein the solution is in direct contact with the interior surface of the casing wall and flowable out of the distal cavity following separation of the lid from the casing body; and
   wherein the second size is larger than the first size.

2. The needle assembly of claim 1, wherein a spout projects radially outwardly at the distal cavity to facilitate application of the solution to a patient.

3. The needle assembly according to claim 1, wherein the lid is a thin film comprising a sealing body and a tab projecting from the sealing body; said tab being sized and shaped to provide a gripping surface for a user to peel the lid from the protective cap prior to application of the solution.

4. The needle assembly of claim 3, wherein the tab has a rough texture on opposite surfaces of the tab.

5. The needle assembly according to claim 1, wherein the lid comprises a cover removably attached to the rim at the second opening and a handle extending from an outside surface of the cover.

6. The needle assembly of claim 5, wherein the handle comprises a gripping surface having a rough texture to facilitate gripping.

7. The needle assembly according to claim 1, wherein a base of the lid is scallop shaped to enable scooping of the solution out from the distal cavity.

8. The needle assembly of claim 1, wherein the body comprises one or more viewing slots at a distal section.

9. The needle assembly of claim 8, further comprising a plurality of pouring spouts at the second opening.

10. The needle assembly of claim 1, wherein the solution is a topical skin adhesive.

11. The needle assembly of claim 10, wherein the topical skin adhesive is a HISTOACRYL® adhesive.

12. A protective cap positioned with a needle device, the protective cap comprising:
   a casing having a casing wall defining a body and the casing wall comprising an exterior surface and an interior surface;
   a first opening at a proximal end of the body, a proximal cavity defined by the interior surface of the casing wall at the first opening having a needle having a needle tip located therein, a second opening of the body remote from the first opening, a distal cavity defined by the interior surface of the casing wall at the second opening, a continuous barrier formed with the interior surface of the casing wall to separate the distal cavity having a first size from the proximal cavity having a second size, and a rim at the second opening;

a lid removably attached at the second opening to seal in and store a quantity of an adhesive solution inside the distal cavity;

wherein the adhesive solution is in direct contact with the interior surface of the casing wall and flowable out of from the distal cavity following separation of the lid from the casing body; and wherein the second size is larger than the first size and the continuous barrier is unitarily formed with the casing to define the distal cavity.

13. The protective cap of claim 12, wherein a spout projects radially outwardly at the distal cavity to facilitate application of the adhesive solution to a patient.

14. The protective cap according to claim 12, wherein the lid is a thin film comprising a sealing body and a tab projecting from the sealing body.

15. The protective cap according to claim 12, wherein the lid comprises a cover removably attached to the rim at the second opening, and a handle extending from an outside surface of the cover.

16. The protective cap of claim 15, wherein the handle comprises a gripping surface having a rough texture to facilitate gripping.

17. The protective cap according to claim 12, wherein the distal cavity comprises a wall structure defining a storage holder attached to the casing.

18. The protective cap of claim 12, wherein the adhesive solution is a topical skin adhesive solution.

19. A method of manufacturing a needle assembly, comprising:

forming a catheter hub and attaching a catheter tube having a distal opening to the catheter hub;

coupling a needle hub having a needle having a needle tip to the catheter hub so that the needle tip extends out a distal end of the catheter tube;

placing a protective cap at least partly over the catheter hub and covering the catheter tube and the needle tip, the protective cap comprising:

a casing having a casing wall defining a body and the casing wall comprising an exterior surface and an interior surface;

a first opening at a proximal end of the body, a proximal cavity defined by the interior surface of the casing wall at the first opening having the needle tip and the catheter tube located therein, a second opening of the body remote from the first opening, a distal cavity defined by the interior surface of the casing wall at the second opening, a continuous barrier formed with the interior surface of the casing wall to separate the distal cavity having a first size from the proximal cavity having a second size, and a rim at the second opening, wherein the body is singularly formed with the distal cavity, the proximal cavity, and the continuous barrier; and a lid removably attached at the second opening to seal in a solution inside the distal cavity;

wherein the solution is in direct contact with the interior surface of the casing wall and flowable out of from the distal cavity following separation of the lid from the casing body; and wherein the second size is larger than the first size and the continuous barrier having a planar surface spanning across a diameter of the protective cap.

20. The method of claim 19, further comprising a needle guard located about the needle to cover the needle tip in a used position.

21. The method of claim 19, wherein the solution is a topical skin adhesive.

22. The method of claim 21, wherein the topical skin adhesive is a HISTOACRYL® adhesive.

* * * * *